United States Patent
Hantash

(10) Patent No.: US 7,638,307 B2
(45) Date of Patent: *Dec. 29, 2009

(54) SAMPLE PROCESSING FOR NUCLEIC ACID AMPLIFICATION

(75) Inventor: Feras M. Hantash, Mission Viejo, CA (US)

(73) Assignee: Quest Diagnostics Investments Incorporated, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/395,226

(22) Filed: Feb. 27, 2009

(65) Prior Publication Data

US 2009/0226974 A1 Sep. 10, 2009

Related U.S. Application Data

(63) Continuation of application No. 11/566,169, filed on Dec. 1, 2006, now Pat. No. 7,521,213.

(51) Int. Cl.
*C12P 19/34* (2006.01)
*C12Q 1/68* (2006.01)
*C07H 21/02* (2006.01)
*C07H 21/04* (2006.01)

(52) U.S. Cl. .......................... 435/91.1; 435/6; 435/7.1; 435/7.2; 435/91.2; 536/23.1; 536/24.3

(58) Field of Classification Search .................... 435/6, 435/7.1, 7.2, 91.1, 91.2; 536/23.1, 24.3
See application file for complete search history.

(56) References Cited

U.S. PATENT DOCUMENTS

| 5,470,724 A | 11/1995 | Ahern et al. |
| 5,856,095 A | 1/1999 | Evans et al. |
| 7,521,213 B2 * | 4/2009 | Hantash ..................... 435/91.1 |
| 2004/0038269 A1 | 2/2004 | Birnboim |

FOREIGN PATENT DOCUMENTS

WO  WO 03/104251  12/2003

OTHER PUBLICATIONS

Grossman et al., High density multiplex detection of nucleic acid sequences: Oligonucleotide ligation assay and sequence-coded separation. Nucleic Acids Research 22:4527-34, 1994.
Spitzer et al., Identification of a new cystic fibrosis transmembrane regulator mutation in a severly affected patient. Eur. Respir. J 19:374-6, 2002.

* cited by examiner

*Primary Examiner*—Jezia Riley
(74) *Attorney, Agent, or Firm*—Foley & Lardner LLP

(57) ABSTRACT

Methods are described for the processing of biological samples for direct use in nucleic acid amplification without extracting or isolating the nucleic acids from the sample. In preferred embodiments, the processed sample provides the nucleic acid template in PCR-based assays.

15 Claims, No Drawings

SEQUENCE LISTING

<160> NUMBER OF SEQ ID NOS: 30

<210> SEQ ID NO 1
<211> LENGTH: 44
<212> TYPE: DNA
<213> ORGANISM: Artificial Sequence
<220> FEATURE:
<223> OTHER INFORMATION: Description of Artificial Sequence: Synthetic primer

<400> SEQUENCE: 1
gcggtcccaa aagggtcagt tgtctttgaa accctatgaa cctg     44

<210> SEQ ID NO 2
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gcggtcccaa aagggtcagt tgtaggaacc atcggacaca tg                         42

<210> SEQ ID NO 3
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gcggtcccaa aagggtcagt tgctccacac ccaggtccac acatt                      45

<210> SEQ ID NO 4
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gcggtcccaa aagggtcagt tggtatagta tactaaaaaa ttaagacagc taaac           55

<210> SEQ ID NO 5
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gcggtcccaa aagggtcagt tgaatccctg atgtcattct tcatagtatt t               51

<210> SEQ ID NO 6
<211> LENGTH: 53
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gcggtcccaa aagggtcagt tgcatccatt acattttcag gctttagcat aat             53

<210> SEQ ID NO 7
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ttcacttttc aatcaactta agtgtaaatg tatgatttta tgcaggttt                  49

<210> SEQ ID NO 8

```
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
cttttcatca ataatcttac ctttaactac actgtgtccc cggtctg                 47

<210> SEQ ID NO 9
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
tacactttaa acttactaca ctaaaatttg acatgatttg ggatagagga              50

<210> SEQ ID NO 10
<211> LENGTH: 53
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
tacactttct ttctttcttt ctttgggaat tgactgtctt tttgaaaagt tat          53

<210> SEQ ID NO 11
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
tgtaaaacga cggccagtgc ttgcaacaaa gacatttatg t                       41

<210> SEQ ID NO 12
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
caggaaacag ctatgacctt catcgaccac tcgaatgtcc                         40

<210> SEQ ID NO 13
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
tgtaaaacga cggccagtag ggagggtctc actctg                             36

<210> SEQ ID NO 14
<211> LENGTH: 36
```

<212> TYPE: DNA
<213> ORGANISM: Artificial Sequence
<220> FEATURE:
<223> OTHER INFORMATION: Description of Artificial Sequence: Synthetic primer

<400> SEQUENCE: 14
caggaaacag ctatgacccg gacggcattg gtgcac                            36

<210> SEQ ID NO 15
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 15
ataacccata agatgatctg tgccg                                        25

<210> SEQ ID NO 16
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 16
ccccaacgca ttaagcattc caa                                          23

<210> SEQ ID NO 17
<211> LENGTH: 50
<212> TYPE: DNA
<213> ORGANISM: Artificial Sequence
<220> FEATURE:
<223> OTHER INFORMATION: Description of Artificial Sequence: Synthetic primer

<400> SEQUENCE: 17
ggaaggacgc ttgcaagata acagagtgtt cttagccaat ggaatatatg             50

<210> SEQ ID NO 18
<211> LENGTH: 46
<212> TYPE: DNA
<213> ORGANISM: Artificial Sequence
<220> FEATURE:
<223> OTHER INFORMATION: Description of Artificial Sequence: Synthetic primer

<400> SEQUENCE: 18
catatattcc attggctaag aagcaagcgt ccttccctcc ttccct                 46

<210> SEQ ID NO 19
<211> LENGTH: 42
<212> TYPE: DNA
<213> ORGANISM: Artificial Sequence
<220> FEATURE:
<223> OTHER INFORMATION: Description of Artificial Sequence: Synthetic primer

<400> SEQUENCE: 19
tttttttttt catatattcc attggctaag aacactctgt ta                     42

<210> SEQ ID NO 20
<211> LENGTH: 20
<212> TYPE: DNA

```
<213> ORGANISM: Artificial Sequence
<220> FEATURE:
<223> OTHER INFORMATION: Description of Artificial Sequence: Synthetic
      primer

<400> SEQUENCE: 20
aaggagggaa ggacgcttgc                                                   20

<210> SEQ ID NO 21
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
gatgaaccca cagaaaatga tgccag                                            26

<210> SEQ ID NO 22
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
ggaaatgccc cattatttag ccaggag                                           27

<210> SEQ ID NO 23
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
cttgaaggac aaaatacctg tattcctcg                                         29

<210> SEQ ID NO 24
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
cttgaaggac aaaatacctg tattccttg                                         29

<210> SEQ ID NO 25
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
agttgattga aaagtgaa                                                     18

<210> SEQ ID NO 26
<211> LENGTH: 24
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 26
aaaggtaaga ttattgatga aaag                                              24

<210> SEQ ID NO 27
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
ttagtgtagt aagtttaaag tgta                                              24

<210> SEQ ID NO 28
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
aaagaaagaa agaaagaaag tgta                                              24

<210> SEQ ID NO 29
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
gtcatccgtg catctttctt ggcatt                                            26

<210> SEQ ID NO 30
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
ctgccattct tcattttacc atgacactga t                                      31
```

SAMPLE PROCESSING FOR NUCLEIC ACID AMPLIFICATION

FIELD OF THE INVENTION

The invention relates to the field of diagnostic assays, in particular, nucleic acid amplification-based assays conducted using biological samples.

BACKGROUND OF THE INVENTION

Nucleic acids are used frequently in the clinical setting in, for example, the identification of genetic mutations and in the diagnosis of bacterial and/or viral infections. In general, such methods have used nucleic acids isolated or extracted from biological samples.

The most commonly used method for isolating DNA from a biological sample (e.g., blood) involves lysing the cells contained in the sample with a combination of a proteolytic enzyme and a detergent followed by extracting the mixture with an organic solvent, e.g., phenol and chloroform, so that the DNA enters the aqueous phase and the protein enters the organic phase. The DNA in the aqueous phase is then concentrated by alcohol precipitation and resuspended in a suitable volume for analysis. Such methods are, however, time-consuming and require the use toxic reagents.

Methods of stabilizing DNA in body fluids are known (e.g., U.S. Patent Application Publication No. 2003-104251).

SUMMARY OF THE INVENTION

Provided herein are methods for using biological samples as a source of nucleic acid template in nucleic acid amplification assays without having to extract the nucleic acids from the sample. The biological sample is contacted with a solution that functions to make the nucleic acid in the sample available for use in amplification without the need for extraction of the nucleic acids. The solution will be referred to herein as "nucleic acid processing solution" (NAPS). Such methods require less sample handling and are quicker and more cost-efficient than methods that require nucleic acid extraction.

In a first aspect, there is provided a method for amplifying nucleic acids from a cell sample, wherein the method comprises, contacting the cell sample with a nucleic acid processing solution (NAPS) having a chelating agent, a denaturing agent, and a buffering agent to form a modified cell sample, wherein the NAPS has a pH between about 5 and about 11, and using the modified cell sample as a template in a nucleic acid amplification reaction.

In a second aspect, there is provided a method for amplifying nucleic acids from a cell sample, wherein the method comprises,
contacting the cell sample with a nucleic acid processing solution (NAPS) having a chelating agent, a denaturing agent, and a buffering agent to form a modified cell sample, wherein the NAPS has a pH between about 5 and about 11, and wherein the modified cell sample provides the template nucleic acids, and
amplifying the template nucleic acids, wherein the template nucleic acids have not been extracted from the modified cell sample.

In a third aspect, there is provided a method for amplifying nucleic acids from an acellular body fluid sample, wherein the method comprises, contacting the acellular body fluid sample with a nucleic acid processing solution (NAPS) having a chelating agent, a denaturing agent, and a buffering agent to form a modified acellular body fluid sample, wherein the NAPS has a pH between about 5 and about 11, and using the modified acellular body fluid sample as a template in a nucleic acid amplification reaction.

In a fourth aspect, there is provided a method for amplifying nucleic acids from an acellular body fluid sample, wherein the method comprises,
contacting the acellular body fluid sample with a nucleic acid processing solution (NAPS) having a chelating agent, a denaturing agent, and a buffering agent to form a modified acellular body fluid sample, wherein the NAPS has a pH between about 5 and about 11, and wherein the modified acellular body fluid sample provides the template nucleic acids, and
amplifying the template nucleic acids, wherein the template nucleic acids have not been extracted from the modified acellular body fluid sample.

In particular embodiments, the NAPS has a pH from about 5.0 and about 11.0, preferably about 6.0 to about 11.0, preferably 7.5 to about 10.0, and more preferably about 7.0. In embodiments wherein DNA is the template for direct PCR, a pH from about 7.0 to about 10.0, or about 7.5, about 8.0, or about 8.0 to about 9.0 can be used. In embodiments wherein RNA is the template for direct or indirect PCR (e.g., RT-PCR), a pH from about 5.0 to about 7.0, desirably from about 6.5 to about 6.8 can be used. A buffer can be added to the NAPS to maintain the pH in a constant range. Such buffers are well-known in the art and include HEPES, TRIS, carbonate buffer, or BES.

The NAPS includes one or more chelating agents to form complexes with metal ions. Without wishing to be bound thus, it is believed that the chelating agent prevents metal ions from binding to DNA, removes metal ions that have already bound to DNA, or bind to metal ions (e.g., Fe(II)/Fe(III) or Cu(I)/Cu(II)) strongly enough to inhibit their redox cycling, and hence, the formation of reactive oxygen species. The chelating agent can be selected from the group consisting of: ethylenediamine tetraacetic acid (EDTA), cyclohexane diaminetetraacetate (CDTA), diethylenetriamine pentaacetic acid (DTPA), tetraazacyclododecanetetraacetic acid (DOTA), tetraazacyclotetradecanetet-raacetic acid (TETA), and desferrioximine, or chelator analogs thereof. Desirably, the chelating agent is cyclohexane diaminetetraacetate (CDTA), diethylenetriamine pentaacetic acid (DTPA), tetraazacyclododecanetetraace-tic acid (DOTA), and desferrioximine, and most desirably, the chelating agent is cyclohexane diaminetetraacetate (CDTA). Stronger chelators (i.e., chelators with a higher dissociation constant than EDTA when bound to a metal) include, but are not limited to, CDTA, DTPA, DOTA, TETA, and desferioximine, or chelator analogs thereof may be used in the NAPS as the only chelating agent or may be used in combination with another chelating agent. The amount or concentration of the chelating agent will depend upon its affinity for metal, which may need to be determined empirically. For CDTA, concentrations in the 1-20 mM range are sufficient, however other concentrations would work.

The NAPS includes one or more denaturing agents such as a detergent, chaotrope, or alcohol. Preferred denaturing agents can be selected from the group consisting of: urea, sodium dodecyl sulfate, dodecyl sulfate, guanidinium chloride, guanidinium thiocyanate, perchlorate, and an alcohol. Preferably, the denaturing agent is urea, dodecyl sulfate, or an alcohol, wherein the alcohol is 10%, 20%, 30%, 40%, 50%, or even 60% of the total NAPS volume. Suitable alcohols include methanol, ethanol, n-propanol, isopropanol, n-butanol, trifluoroethanol, phenol, or 2,6-di-tert-butyl-4-methylphenol.

In certain embodiments, the NAPS further comprises one or more reducing agents. Suitable reducing agents include ascorbic acid, dithionite, erythiorbate, N-acetylcysteine, cysteine, glutathione, dithiothreitol, 2-mercaptoethanol, dierythritol, a resin-supported thiol, a resin-supported phosphine, vitamin E, and trolox, or salts thereof. Preferably, the reducing agent is ascorbic acid, erythiorbate, N-acetylcysteine, dithiothreitol, or 2-mercaptoethanol, and more preferably, the reducing agent is ascorbic acid or 2-mercaptoethanol. In particular embodiments, the concentration of the reducing agent in the NAPS is greater than or equal to 50 millimolar. Antioxidant free-radical scavengers are also useful as reducing agents. Examples include antioxidant vitamins, antioxidant hormones, antioxidant enzymes, thiols, and phenols.

In some embodiments, the NAPS may further comprise an antimicrobial agent. "Antimicrobial agent" as used herein refers to a substance that reduces the rate of growth of a microbial organism compared to the rate of growth of the microbe in the absence of that substance. A reduction in the rate of growth of a microbe may be by at least 5%, preferably, by at least 10%, more preferably, by at least 20%, at least 50%, or at least 75%, and most preferably, by 90% or more. Antimicrobial agent includes substances that affect the viability, virulence, or pathogenicity of a microbe. An antimicrobial agent can be naturally occurring (e.g., derived or obtained from bacteria), synthetic, or recombinant. An antimicrobial agent may have static, cidal, or both properties. An antimicrobial agent is static if it inhibits cell division without affecting the viability of the inhibited cell. An antimicrobial agent is cidal if it causes cell death. Cell death is commonly detected by the absence of cell growth in liquid growth medium (e.g., absence of turbidity) or on a solid surface (e.g., absence of colony formation on agar). Those of skill in the art know that a substance or group of substances which is static at a given concentration may be cidal at a higher concentration. Certain static substances are not cidal at any concentration. Preferably, the solution includes an alcohol as an antimicrobial agent, preferably ethanol.

In still other embodiments, the NAPS further includes a ribonuclease inhibitor. Preferred ribonuclease inhibitors are selected from the group consisting of: heparin, heparan sulfate, oligo(vinylsulfonic acid), poly(vinylsulfonic acid), oligo(vinylphosphonic acid), and poly(vinylsulfuric acid), or salts thereof. The inclusion a ribonuclease inhibitor in the solution is particularly preferred when template nucleic acid in the sample is to be RNA, particularly mRNA, or when the template nucleic acid is from a microbe.

As used herein, the term "biological sample" refers to any liquid or solid material that is obtained from a biological source, preferably from an animal, most preferably from a human. A biological sample may be a cell sample or may be an acellular liquid sample. In preferred embodiments, the acellular liquid sample is an acellular body fluid sample.

As used herein, the term "cell sample" includes any source of cells containing nucleic acids that are desired to be used as a template in a nucleic acid amplification reaction. Cells may be prokaryotic or eukaryotic. Eukaryotic cell samples may be animal or plant cells. Preferred eukaryotic cell samples are mammalian cells, preferably human. In some embodiments, a cell sample can be cells in culture or a tissue sample from an animal, most preferably, a human. Tissue samples include, but are not limited to, blood, bone marrow, cell-containing body fluids such as cerebrospinal fluid, or tissue (e.g., biopsy material). Preferred samples include whole blood or white blood cells (WBC). Cell samples may be packed cells or cells suspended in liquid.

The terms "body fluid" or "bodily fluid" are used interchangeably herein and refer to a fluid sample from a human or other animal. Body fluids include, but are not limited to amniotic fluid, blood, cerebrospinal fluid, peritoneal fluid, plasma, pleural fluid, saliva, semen, serum, sputum, tears, and urine. Body fluids may be cell-containing or may be acellular.

As used herein "acellular body fluid" refers to a body fluid lacking cells. Such acellular body fluids are generally produced by processing a cell-containing body fluid by, for example, centrifugation or filtration, to remove the cells. Acellular body fluid, however, may contain cell fragments or cellular debris. Preferred acellular body fluids are plasma and serum.

As used herein "modified biological sample" or "modified sample" are used interchangeably and refers to a biological sample that has been processed so that the nucleic acids contained therein may be directly amplified by a standard nucleic acid amplification method. Nucleic acids in a modified biological sample need not be extracted from the sample. Preferably, modified biological samples are the result of contacting a biological sample with a NAPS comprising a chelating agent, a denaturing agent, and a buffering agent, as described herein. Modified samples include modified cell samples and modified acellular body fluid samples.

As used herein "modified cell sample" refers to a cell sample that has been processed so that the nucleic acids contained therein may be directly amplified by a standard nucleic acid amplification method. Nucleic acids in a modified cell sample need not be extracted from the sample. Preferably, modified cell samples are the result of contacting a cell sample with a NAPS comprising a chelating agent, a denaturing agent, and a buffering agent, as described herein.

As used herein "modified acellular body fluid sample" refers to an acellular body fluid sample that has been processed so that the nucleic acids contained therein may be directly amplified by a standard nucleic acid amplification method. Nucleic acids in a modified acellular body fluid sample need not be extracted from the sample. Preferably, modified acellular body fluid samples are the result of contacting an acellular body fluid sample with a NAPS comprising a chelating agent, a denaturing agent, and a buffering agent, as described herein.

As used herein, "nucleic acid" refers broadly to genomic DNA, segments of a chromosome, segments or portions of DNA, cDNA, and/or RNA. Nucleic acid may be derived or obtained from an originally isolated nucleic acid sample from any source (e.g., isolated from, purified from, amplified from, cloned from, reverse transcribed from sample DNA or RNA). Nucleic acids include those resident in a biological sample, preferably a cell sample or an acellular body fluid sample.

As used herein the term "extracted" used in reference to nucleic acids in a cell sample means that the nucleic acids have been physically separated from cells containing the nucleic acid by addition of a sufficient volume of organic solvent to lyse the cells and separate the protein from the nucleic acids, wherein the nucleic acid in the aqueous phase is separated from the protein. The nucleic acids in the aqueous phase can be concentrated by addition of a sufficient volume of ethanol to precipitate the nucleic acids. Other methods of extracting nucleic acids include the capture of nucleic acids on solid phase using, for example, an oligonucleotide-coupled bead (e.g., oligo-dT). When used in reference to nucleic acids in an acellular body fluid, extracted means that the nucleic acids have not been separated from the sample by, for example, alcohol precipitation.

In some embodiments, the method may include a centrifugation step. For example, a centrifugation step may be used to concentrate the cells of the cell sample prior to the addition of NAPS. In another example, a centrifugation step may be used to remove cellular debris from a modified cell sample. Such a centrifugation step is not considered an extraction of nucleic acids.

"Genomic nucleic acid" or "genomic DNA" refers to some or all of the DNA from the nucleus of a cell. Genomic DNA may be intact or fragmented (e.g., digested with restriction endonucleases by methods known in the art). In some embodiments, genomic DNA may include sequence from all or a portion of a single gene or from multiple genes, sequence from one or more chromosomes, or sequence from all chromosomes of a cell. In contrast, the term "total genomic nucleic acid" is used herein to refer to the full complement of DNA contained in the genome of a cell. As is well known, genomic nucleic acid includes gene coding regions, introns, 5' and 3' untranslated regions, 5' and 3' flanking DNA and structural segments such as telomeric and centromeric DNA, replication origins, and intergenic DNA.

As used herein, the term "hybridize" or "specifically hybridize" refers to a process where two complementary nucleic acid strands anneal to each other under appropriately stringent conditions. Hybridizations are typically and preferably conducted with probe-length nucleic acid molecules, preferably 20-100 nucleotides in length. Nucleic acid hybridization techniques are well known in the art. See, e.g., Sambrook, et al., 1989, Molecular Cloning: A Laboratory Manual, Second Edition, Cold Spring Harbor Press, Plainview, N.Y. Those skilled in the art understand how to estimate and adjust the stringency of hybridization conditions such that sequences having at least a desired level of complementarity will stably hybridize, while those having lower complementarity will not. For examples of hybridization conditions and parameters, see, e.g., Sambrook, et al., 1989, Molecular Cloning: A Laboratory Manual, Second Edition, Cold Spring Harbor Press, Plainview, N.Y.; Ausubel, F. M. et al. 1994, Current Protocols in Molecular Biology. John Wiley & Sons, Secaucus, N.J.

The term "amplification" or "amplify" as used herein means one or more methods known in the art for copying a target or template nucleic acid, thereby increasing the number of copies of a selected nucleic acid sequence. Amplification may be exponential or linear. A target or template nucleic acid may be either DNA or RNA. The sequences amplified in this manner form an "amplified region" or "amplicon." While the exemplary methods described hereinafter relate to amplification using the polymerase chain reaction ("PCR"), numerous other methods are known in the art for amplification of nucleic acids (e.g., isothermal methods, rolling circle methods, etc.). The skilled artisan will understand that these other methods may be used either in place of, or together with, PCR methods. See, e.g., Saiki, "Amplification of Genomic DNA" in PCR Protocols, Innis et al., Eds., Academic Press, San Diego, Calif. 1990, pp 13-20; Wharam et al., Nucleic Acids Res. 2001 Jun. 1; 29(11):E54-E54; Hafner et al., Biotechniques 2001 April; 30(4):852-6, 858, 860 passim. Further amplification methods suitable for use with the present methods include, for example, reverse transcription PCR (RT-PCR), ligase chain reaction (LCR), transcription-based amplification system (TAS), nucleic acid sequence based amplification (NASBA) reaction, self-sustained sequence replication (3SR), strand displacement amplification (SDA) reaction, boomerang DNA amplification (BDA), Q-beta replication, or isothermal nucleic acid sequence based amplification.

As used herein, the phrase "using the modified cell sample as a template in a nucleic acid amplification reaction" means that the nucleic acids have not been extracted from the modified cell sample prior to amplifying the template nucleic acids contained therein. Similarly, the phrase "using the modified acellular body fluid sample as a template in a nucleic acid amplification reaction" means that the nucleic acids have not been extracted from the modified acellular body fluid sample prior to amplifying the template nucleic acids contained therein.

"Sense strand" means the strand of double-stranded DNA (dsDNA) that includes at least a portion of a coding sequence of a functional protein. "Anti-sense strand" means the strand of dsDNA that is the reverse complement of the sense strand.

As used herein, a "forward primer" is a primer that anneals to the anti-sense strand of dsDNA. A "reverse primer" anneals to the sense-strand of dsDNA.

As used herein, the term "about" when used in reference to a numerical value, means plus or minus 10%.

The summary of the invention described above is non-limiting and other features and advantages of the invention will be apparent from the following detailed description of the invention, and from the claims.

DETAILED DESCRIPTION OF THE INVENTION

Sample Preparation

The methods of the present invention can be used to prepare biological samples for use in nucleic acid amplification reactions without extracting the nucleic acids from the rest of the sample. This method is achieved by mixing the biological sample with NAPS to form a modified biological sample, which can be used directly as template in an amplification reaction. In preferred embodiments, the biological sample is a cell sample or an acellular body fluid sample.

In some embodiments, NAPS may be added directly to cell samples or may be added to packed cells obtained from cell samples in which the cells have been pelleted by centrifugation. NAPS is added to the cell sample at a ratio of, for example, 1:1, 1:2, 1:3, 1:4, 1:5 or higher of cell sample to NAPS. The actual ratio depends on the cell concentration. In preferred embodiments, the cell sample is whole blood and is mixed with NAPS at a ratio of, for example, 1:1, 1:2, 1:3, 1:4, 1:5, or higher of blood to NAPS. Cell samples in which the cells have been concentrated and thus have a higher density of cells (e.g., a packed cell sample) may require more NAPS than those cell samples in which the cells have not been concentrated. For example, in processing a sample of packed cells, a volume of NAPS equivalent to 2-3 times (or higher) the volume of the packed cells may be used.

In one example, a NAPS of 2% SDS, 10 mM EDTA, and 50 mM Tris-HCl pH 8.0 is added to a sample of blood to prepare the sample for direct use in PCR. In another example, a NAPS of 0.5M NaOAc, 0.2M Tris-HCl, 0.15M sodium ascorbate, 10 mM CDTA, 1% SDS, 30% (v/v) ethanol, pH 9.5 (see PCT International Publication No. WO03104251 at Table 3, lane 1) is added to a sample of blood to prepare the sample for direct use in PCR. In a further example, the NAPS can be the DNA preserving solution contained in the Oragene™ DNA Self-Collection Kit (DNA Genotek, Ottawa, Ontario, Canada). In this case, a blood sample is applied to the sample reservoir, the reservoir is capped, releasing the DNA preserving solution into the chamber containing the blood, thus stabilizing the DNA that is present. The composition of additional NAPS are described in PCT International Publication No. WO03104251 or U.S. Patent Application Publication No. 2003-104251 (see "compositions", at, for example, Table 3).

In other embodiments, NAPS may be added directly to acellular body fluid samples. NAPS is added to the acellular body fluid sample at a ratio of, for example, 1:1, 1:2, 1:3, 1:4, 1:5 or higher of acellular body fluid sample to NAPS. The actual ratio may depend on the type of acellular body fluid and the concentration of nucleic acids contained therein. In preferred embodiments, the acellular body fluid sample is plasma and is mixed with NAPS at a ratio of, for example, 1:1, 1:2, 1:3, 1:4, 1:5, or higher of plasma to NAPS.

In one example, a NAPS of 2% SDS, 10 mM EDTA, and 50 mM Tris-HCl pH 8.0 is added to a sample of plasma to prepare the sample for direct use in PCR. In another example, a NAPS of 0.5M NaOAc, 0.2M Tris-HCl, 0.15M sodium ascorbate, 10 mM CDTA, 1% SDS, 30% (v/v) ethanol, pH 9.5 (see PCT International Publication No. WO03104251 at Table 3, lane 1) is added to a sample of plasma to prepare the sample for direct use in PCR. In a further example, the NAPS can be the DNA preserving solution contained in the Oragene™ DNA Self-Collection Kit (DNA Genotek, Ottawa, Ontario, Canada). In this case, a plasma sample is applied to the sample reservoir, the reservoir is capped, releasing the DNA preserving solution into the chamber containing the plasma, thus stabilizing the DNA that is present. The composition of additional NAPS are described in PCT International Publication No. WO03104251 or U.S. Patent Application Publication No. 2003-104251 (see "compositions", at, for example, Table 3).

Following addition of the NAPS, the resulting modified sample may be further treated with an optional Purifier solution (DNA Genotek, Ottawa, Ontario, Canada).

The modified sample may be optionally centrifuged and the supernatant used as template in amplification methods.

The modified samples processed as described above may desirably be diluted in water or an appropriate buffer for optimal use as a template in an amplification reaction. The skilled artisan will recognize that the dilution factor may vary with sample type and amplification method. For example, undiluted modified samples may be too concentrated for optimal amplification of nucleic acid. Similarly, modified samples that are highly diluted may have too low of a concentration of template for optimal amplification. Preferred dilutions include, but are not limited to, ratios of 1:5, 1:10, 1:25, 1:50, 1:100, 1:125, or higher of sample to water or dilution buffer. The skilled artisan will further understand that a minimal amount of testing may be needed to determine the optimal dilution factor for the specific sample used.

Amplification of Nucleic Acids

As detailed herein, the addition of NAPS to a biological sample results in a modified biological sample, which can be directly used as a source of template in amplification methods. In preferred embodiments, template nucleic acids may be amplified from modified biological samples using PCR or RT-PCR, however, the skilled artisan will understand that numerous methods are known in the art for amplification of nucleic acids, and that these methods may be used either in place of, or together with, PCR. Nucleic acid amplification methods, such as PCR, RT-PCR, isothermal methods, rolling circle methods, etc., are well known to the skilled artisan. See, e.g., Saiki, "Amplification of Genomic DNA" in PCR Protocols, Innis et al., Eds., Academic Press, San Diego, Calif. 1990, pp 13-20; Wharam et al., Nucleic Acids Res. 2001 Jun. 1; 29(11):E54-E54; Hafner et al., Biotechniques 2001 April; 30(4):852-6, 858, 860 passim; Zhong et al., Biotechniques 2001 April; 30(4):852-6, 858, 860 passim.

Amplification methods suitable for use with the present methods include, for example, polymerase chain reaction (PCR), reverse transcription PCR(RT-PCR), ligase chain reaction (LCR), transcription-based amplification system (TAS), nucleic acid sequence based amplification (NASBA) reaction, self-sustained sequence replication (3SR), strand displacement amplification (SDA) reaction, boomerang DNA amplification (BDA), Q-beta replication: or isothermal nucleic acid sequence based amplification. These methods of amplification each described briefly below and are well-known in the art.

PCR is a technique for making many copies of a specific template DNA sequence. The reaction consists of multiple amplification cycles and is initiated using a pair of primer oligonucleotides that hybridize to the 5' and 3' ends of the sequence to be copied. The amplification cycle includes an initial denaturation, and up to 50 cycles of annealing, strand elongation (or extension) and strand separation (denaturation). In each cycle of the reaction, the DNA sequence between the primers is copied. Primers can bind to the copied DNA as well as the original template sequence, so the total number of copies increases exponentially with time. PCR can be performed as according to Whelan, et al, *Journal of Clinical Microbiology*, 33(3):556-561 (1995). Briefly, a PCR reaction mixture includes two specific primers, dNTPs, approximately 0.25 U of Taq polymerase, and 1×PCR Buffer, which is amplified using a thermal cycler. Cycling parameters can be varied, depending on, for example, the melting temperature of the primer or the length of nucleic acids to be extended. The skilled artisan is capable of designing and preparing primers that are appropriate for amplifying a target sequence. The length of the amplification primers for use in the present invention depends on several factors including the nucleotide sequence identity and the temperature at which these nucleic acids are hybridized or used during in vitro nucleic acid amplification. The considerations necessary to determine a preferred length for an amplification primer of a particular sequence identity are well-known to a person of ordinary skill and include considerations described herein. For example, the length of a short nucleic acid or oligonucleotide can relate to its hybridization specificity or selectivity.

Real time PCR is PCR-based amplification method in which PCR products are detected in real time, that is, the accumulation of PCR products can be determined at each cycle. Real Time PCR is performed using TaqMan® probes in combination with a suitable amplification/analyzer such as Applied Biosystems (ABI) Prism 7900HT Sequence Detection System, which is a high-throughput real-time PCR system. Briefly, TaqMan™ probes specific for the amplified target sequence are included in the PCR amplification reaction. These probes contain a reporter dye at the 5' end and a quencher dye at the 3' end. Probes hybridizing to different target sequences are conjugated with a different fluorescent reporter dye. In this way, more than one target sequence can be assayed for in the same reaction vessel. During PCR, the fluorescently labeled probes bind specifically to their respective target sequences; the 5' nuclease activity of Taq polymerase cleaves the reporter dye from the probe and a fluorescent signal is generated. The increase in fluorescence signal is detected only if the target sequence is complementary to the probe and is amplified during PCR. A mismatch between probe and target greatly reduces the efficiency of probe hybridization and cleavage. The ABI Prism 7700HT or 7900HT Sequence detection System measures the increase in fluorescence during PCR thermal cycling, providing "real time" detection of PCR product accumulation. Real Time detection on the ABI Prism 7900HT or 7900HT Sequence Detector monitors fluorescence and calculates Rn during each PCR cycle. The threshold cycle, or Ct value, is the cycle at which fluorescence intersects the threshold value. The threshold value is determined by the sequence detection system software or manually.

"RT-PCR" as used herein refers to the combination of reverse transcription and PCR in a single assay. "Reverse transcription" is a process whereby an RNA template is transcribed into a DNA molecule by a reverse transcriptase enzyme. Thus, "reverse transcriptase" describes a class of polymerases characterized as RNA-dependent DNA polymerases, that is, such polymerases use an RNA template to synthesize a DNA molecule. Historically, reverse transcriptases have been used to reverse-transcribe mRNA into cDNA. However, reverse transcriptases can be used to reverse-transcribe other types of RNAs such as viral genomic RNA or viral sub-genomic RNA. Standard reverse transcriptases include Maloney Murine Leukemia Virus Reverse Transcriptase (MoMuLV RT) and Avian myoblastosis virus (AMV). These enzymes have 5'->3' RNA-dependent DNA polymerase activity, 5'->3' DNA-dependent DNA polymerase activity, and RNase H activity. However, unlike many DNA-dependent DNA polymerases, these enzymes lack 3'->5' exonuclease activity necessary for "proofreading," (i.e., correcting errors made during transcription). After a DNA copy of an RNA has been prepared, the DNA copy may be subjected to various DNA amplification methods such as PCR.

LCR is a method of DNA amplification similar to PCR, except that it uses four primers instead of two and uses the enzyme ligase to ligate or join two segments of DNA. LCR can be performed as according to Moore et al., *Journal of Clinical Microbiology* 36(4):1028-1031 (1998). Briefly, an LCR reaction mixture contains two pair of primers, dNTP, DNA ligase and DNA polymerase representing about 90 µl, to which is added 100 µl of isolated nucleic acid from the target organism. Amplification is performed in a thermal cycler (e.g., LCx of Abbott Labs, North Chicago, Ill.).

TAS is a system of nucleic acid amplification in which each cycle is comprised of a cDNA synthesis step and an RNA transcription step. In the cDNA synthesis step, a sequence recognized by a DNA-dependent RNA polymerase (i.e., a polymerase-binding sequence or PBS) is inserted into the cDNA copy downstream of the target or marker sequence to be amplified using a two-domain oligonucleotide primer. In the second step, an RNA polymerase is used to synthesize multiple copies of RNA from the cDNA template. Amplification using TAS requires only a few cycles because DNA-dependent RNA transcription can result in 10-1000 copies for each copy of cDNA template. TAS can be performed according to Kwoh et al., *PNAS* 86:1173-7 (1989). Briefly, extracted RNA is combined with TAS amplification buffer and bovine serum albumin, dNTPs, NTPs, and two oligonucleotide primers, one of which contains a PBS. The sample is heated to denature the RNA template and cooled to the primer annealing temperature. Reverse transcriptase (RT) is added the sample incubated at the appropriate temperature to allow cDNA elongation. Subsequently T7 RNA polymerase is added and the sample is incubated at 37° C. for approximately 25 minutes for the synthesis of RNA. The above steps are then repeated. Alternatively, after the initial cDNA synthesis, both RT and RNA polymerase are added following a 1 minute 100° C. denaturation followed by an RNA elongation of approximately 30 minutes at 37° C. TAS can be also be performed on solid phase as according to Wylie et al., *Journal of Clinical Microbiology*, 36(12):3488-3491 (1998). In this method, nucleic acid targets are captured with magnetic beads containing specific capture primers. The beads with captured targets are washed and pelleted before adding amplification reagents which contains amplification primers, dNTP, NTP, 2500 U of reverse transcriptase and 2500 U of T7 RNA polymerase. A 100 µl TMA reaction mixture is placed in a tube, 200 µl oil reagent is added and amplification is accomplished by incubation at 42° C. in a waterbath for one hour.

NASBA is a transcription-based amplification method which amplifies RNA from either an RNA or DNA target. NASBA is a method used for the continuous amplification of nucleic acids in a single mixture at one temperature. For example, for RNA amplification, avian myeloblastosis virus (AMV) reverse transcriptase, RNase H and T7 RNA polymerase are used. This method can be performed as according to Heim, et al., *Nucleic Acids Res.*, 26(9):2250-2251 (1998). Briefly, an NASBA reaction mixture contains two specific primers, dNTP, NTP, 6.4 U of AMV reverse transcriptase, 0.08 U of *Escherichia coli* Rnase H, and 32 U of T7 RNA polymerase. The amplification is carried out for 120 min at 41° C. in a total volume of 201.

In a related method, self-sustained sequence-replication (3SR) reaction, isothermal amplification of target DNA or RNA sequences in vitro using three enzymatic activities: reverse transcriptase, DNA-dependent RNA polymerase and *Escherichia coli* ribonuclease H. This method may be modified from a 3-enzyme system to a 2-enzyme system by using human immunodeficiency virus (HIV)-1 reverse transcriptase instead of avian myeloblastosis virus (AMV) reverse transcriptase to allow amplification with T7 RNA polymerase but without *E. coli* ribonuclease H. In the 2-enzyme 3SR, the amplified RNA is obtained in a purer form compared with the 3-enzyme 3SR (Gebinoga & Oehlenschlager *European Journal of Biochemistry*, 235:256-261, 1996).

SDA is an isothermal nucleic acid amplification method. A primer containing a restriction site is annealed to the template. Amplification primers are then annealed to 5' adjacent sequences (forming a nick) and amplification is started at a fixed temperature. Newly synthesized DNA strands are nicked by a restriction enzyme and the polymerase amplification begins again, displacing the newly synthesized strands. SDA can be performed as according to Walker, et al., *PNAS*, 89:392-6 (1992). Briefly, an SDA reaction mixture contains four SDA primers, dGTP, dCTP, TTP, dATP, 150 U of Hinc II, and 5 U of exonuclease-deficient of the large fragment of *E. coli* DNA polymerase I (exo⁻ Klenow polymerase). The sample mixture is heated 95° C. for 4 minutes to denature target DNA prior to addition of the enzymes. After addition of the two enzymes, amplification is carried out for 120 min. at 37° C. in a total volume of 50 µl. Then, the reaction is terminated by heating for 2 minutes at 95° C.

Boomerang DNA amplification (BDA) is a method in which the polymerase begins extension from a single primer-binding site and then makes a loop around to the other strand, eventually returning to the original priming site on the DNA. BDA is differs from PCR through its use of a single primer. This method involves an endonuclease digestion of a sample DNA, producing discrete DNA fragments with sticky ends, ligating the fragments to "adapter" polynucleotides (comprised of a ligatable end and first and second self-complementary sequences separated by a spacer sequence) thereby forming ligated duplexes. The ligated duplexes are denatured to form templates to which an oligonucleotide primer anneals at a specific sequence within the target or marker sequence of interest. The primer is extended with a DNA polymerase to form duplex products followed by denaturation of the duplex products. Subsequent multiple cycles of annealing, extending, and denaturing are performed to achieve the desired degree of amplification (U.S. Pat. No. 5,470,724).

The Q-beta replication system uses RNA as a template. Q-beta replicase synthesizes the single-stranded RNA genome of the coliphage Qβ. Cleaving the RNA and ligating in a nucleic acid of interest allows the replication of that sequence when the RNA is replicated by Q-beta replicase (Kramer & Lizardi *Trends Biotechnol.* 1991 9(2):53-8, 1991).

A variety of amplification enzymes are well known in the art and include, for example, DNA polymerase, RNA polymerase, reverse transcriptase, Q-beta replicase, thermostable DNA and RNA polymerases. Because these and other amplification reactions are catalyzed by enzymes, in a single step assay that the nucleic acid releasing reagents and the detection reagents should not be potential inhibitors of amplification enzymes if the ultimate detection is to be amplification based.

Amplified nucleic acid product may be detected by any of a variety of well-known methods, for example, electrophoresis (e.g., gel electrophoresis or capillary electrophoresis). Amplified fragments may be subjected to further methods of detecting, for example, variant sequences (e.g., single nucleotide polymorphisms (SNPs)). An exemplary method is single nucleotide primer extension (Lindblad-Toh et al., Large-scale discovery and genotyping of single-nucleotide polymorphisms in the mouse. Nature Genet. 2000 April; 24(4):381-6). In this reaction, an oligonucleotide primer is designed to have a 3' end that is one nucleotide 5' to a specific mutation site. In some embodiments, the extension primers are labeled with a tag or a member of a binding pair to allow the capture of the primer on solid phase. In particular embodiments, the primers may be tagged with varying lengths of nonspecific polynucleotides (e.g., poly-GACT) to allow multiplex detection of preferably 2 or more, more preferably 3 or more, 4 or more, 5 or more, even 10 or more different mutations (polymorphisms) in a single reaction. The primer hybridizes to the PCR amplicon in the presence of one or more labeled ddNTPs and a DNA polymerase. The polymerase extends the primer by one nucleotide, adding a single, labeled ddNTP to the 3' end of the extension primer. The addition of a dideoxy nucleotide terminates chain elongation. If more than one dideoxynucleotide (e.g., ddATP, ddGTP, ddCTP, ddTTP, ddUTP, etc.) is used in a reaction, one or more can be labeled. If multiple labels are used, the labels can be distinguishable e.g., each is labeled with a different fluorescent colored dye. The products are labeled oligonucleotides, each one of which may be detected based on its label. Further methods of detecting variant sequences include the READIT SNP Genotyping System (Promega Corporation, Madison Wis.) and oligonucleotide ligation assays.

The following examples serve to illustrate the present invention. These examples are in no way intended to limit the scope of the invention.

Example 1

TPMT Mutation Detection Assay Using Processed Whole Blood as the Nucleic Acid Template for Amplification Processed whole blood samples provided the template for a triplex PCR reaction used to amplify three regions of the TPMT gene each containing one of the three mutation sites of interest (i.e., G238C, G460A, and A719G). The amplification reaction was followed by two single nucleotide primer extension reactions to detect the presence of mutations.

Whole blood samples were prepared for use in the TPMT assay by the following two methods:

A) A 30 μL aliquot of a blood sample was mixed with 90 μL of NAPS consisting of 2% SDS, 50 mM Tris-HCl, pH 8.0, 10 mM EDTA. The resulting solution was diluted 1:125 with water prior to use as template in PCR.

B) A 30 μL aliquot of a blood sample was mixed with 90 μL of DNA preserving solution from the Oragene™ DNA Self-Collection Kit (DNA Genotek, Ottawa, Ontario, Canada). The mixture was incubated at 65° C. for approximately 30 minutes. 60 μL H$_2$O was added and the solution mixed and centrifuged at 5000 rpm for 5 minutes. A 30 μL aliquot was removed from the upper portion of the liquid following centrifugation, transferred to a fresh plate, and diluted 1:25-1:125 prior use as template in PCR.

PCR was conducted using the following amplification primers.

TABLE 1

TPMT amplification primers containing a universal linker sequence

| Primer Location in TPMT Gene | Primer Name | Primer Sequence | Position in GenBank Accession No. AB045146 |
|---|---|---|---|
| Exon 5 | TPMT-E5F-Linker | 5'GCGGTCCCAAAAGGGTCAGT TGTCTTTGAAACCCTATGAACC TG-3' (SEQ ID NO:1) | 12089-12110 |
| Intron 5 | TPMT-5R-Linker | 5'GCGGTCCCAAAAGGGTCAGT TGTAGGAACCATCGGACACAT G-3' (SEQ ID NO:2) | 12435-12454 |
| Intron 6 | TPMT-I6F-Linker | 5'GCGGTCCCAAAAGGGTCAGT TGCTCCACACCCAGGTCCACAC ATT-3' (SEQ ID NO:3) | 16753-16775 |
| Intron 7 | TPMT-I7R-Linker | 5'GCGGTCCCAAAAGGGTCAGT TGGTATAGTATACTAAAAAATT AAGACAGCTAAAC-3' (SEQ ID NO:4) | 17010-17042 |
| Intron 9 | TPMT-I9F-Linker | 5'GCGGTCCCAAAAGGGTCAGT TGAATCCCTGATGTCATTCTTC ATAGTATTT-3' (SEQ ID NO:5) | 25122-25150 |
| Exon 10 | TPMT-R971-Linker | 5'GCGGTCCCAAAAGGGTCAGT TGCATCCATTACATTTTCAGGC TTTAGCATAAT-3' (SEQ ID NO:6) | 25342-25372 |

Universal linker portion of each primer shown in bold

A 5× solution of TPMT primer mix was prepared according to table 2 below.

TABLE 2

5X solution of TPMT primer mix

| Primer (50 μM) | Volume (μL) | Concentration 5X solution (μM) | Concentration Final solution (μM) |
|---|---|---|---|
| TPMT-E5F-linker (SEQ ID NO:1) | 144 | 1.25 | 0.25 |
| TPMT-5R-linker (SEQ ID NO:2) | 144 | 1.25 | 0.25 |
| TPMT-I6F-linker (SEQ ID NO:3) | 230 | 2.00 | 0.40 |

TABLE 2-continued 5X solution of TPMT primer mix

| Primer (50 µM) | Volume (µL) | Concentration 5X solution (µM) | Concentration Final solution (µM) |
|---|---|---|---|
| TPMT-I7R-linker (SEQ ID NO:4) | 230 | 2.00 | 0.40 |
| TPMT-I9F-linker (SEQ ID NO:5) | 173 | 1.50 | 0.30 |
| TPMT-R971-linker (SEQ ID NO:6) | 173 | 1.50 | 0.30 |
| dH₂O | 4,666 | | |
| Total | 5,760 | | |

The TPMT PCR master mix was prepared according to table 3 below.

TABLE 3

TPMT PCR master mix

| Components | Per Rxn (µL) | x3000 (µL) |
|---|---|---|
| 10X Roche PCR Buffer | 2.5 | 7,500 |
| 25 mM dNTP mix | 0.25 | 750 |
| 5X TPMT primer mix | 5.0 | 15,000 |
| 25 mM MgCl₂ | 1.0 | 3,000 |
| Sterile H₂O | 14.0 | 42,000 |
| Total | 22.75 | 68,250 |

A 25 µL reaction containing 22.75 µL TPMT master mix, 0.25 µL Taq polymerase (HotStarTaq) and 2 µL of the genomic DNA-containing test sample or control DNA was run under the following PCR conditions.

TABLE 4

PCR amplification conditions

| Step | Temperature | Time |
|---|---|---|
| 1 | 95° C. | 15 min. |
| 2 | 94° C. | 30 sec |
| 3 | 60° C. | 60 sec. |
| 4 | 70° C. | 30 sec. |
| 5 | go to step 2 | 34 cycles* |
| 6 | 70° C. | 7 min. |
| 7 | 4° C. | Hold |

After PCR was complete, the samples were treated with SAP (shrimp alkaline phosphatase) and Exo I (exonuclease I). A fresh SAP/ExoI cocktail was prepared prior to each use according to table 5 below.

TABLE 5

SAP/ExoI cocktail

| Reagent | Volume (µL) for 1 reaction | Volume (µL) for 120 rxns (full plate) |
|---|---|---|
| SAP (1 unit/µL) | 7.5 | 900 |
| Exo I (10 unit/µL) | 0.3 | 36 |
| Sterile H₂O | 14.7 | 1,764 |
| Total | 22.5 | 2,700 |

22.5 µL of the SAP/ExoI cocktail was dispensed into each well of a 96-well plate. 7.5 µL of PCR product was added to each well. The samples were incubated at 37° C. for 2 hours, 75° C. for 15 minutes then chilled to 4° C. and stored at 2-8° C. until use.

Single Nucleotide Primer Extension

Two single nucleotide primer extension reactions (termed "the A reaction" and "the G reaction") were performed on the SAP/ExoI treated samples. The A reaction contains extension primers and labeled ddATP to allow the detection of mutation at position 460 (i.e., G460A) and the wild-type nucleotide at position 719. The G reaction contains extension primers and labeled ddGTP to allow the detection of mutation at position 238 of the antisense strand and the wild-type at position 238 of the sense strand. The G reaction further permits the detection of the wild-type nucleotide at position 460 and the mutation at position 460. The extension primers used in both the A reaction and the G reaction are as follows.

TABLE 6

Exemplary extension primers containing an oligonucleotide tag

| Mutation | Primer name | Primer Sequence | Position in GenBank Accession No. AB045146 |
|---|---|---|---|
| G238C Sense strand | 2AF Tag | 5'TTCACTTTTCAATCAACTT AAGTGTAAATGTATGATTTTA TGCAGGTTT-3' (SEQ ID NO:7) | 12194-12224 |
| G238C Antisense strand | 2AR Tag | 5'CTTTTCATCAATAATCTTA CCTTTAACTACACTGTGTCCC CGGTCTG-3' (SEQ ID NO:8) | 12226-12248 |
| G460A | 3A1F Tag | 5'TACACTTTAAACTTACTAC ACTAAAATTTGACATGATTTG GGATAGAGGA-3' (SEQ ID NO:9) | 16928-16953 |
| A719G | 3A2F Tag | 5'TACACTTTCTTTCTTTCTT TCTTTGGGAATTGACTCGTCT TTTTGAAAAGTTAT-3' (SEQ ID NO:1) | 25241-25269 |

Oligonucleotide tag portion of the primer shown in bold

A Reaction

The primer extension (PE) primer master mix for the A reaction was prepared according to table 7 below.

TABLE 7

Primer Extension (PE) Primer Mix for A reaction

| Mutation | Primer | Concentration (µM) | Volume (µL) for 1 rxn | Volume (µL) for 4000 rxns |
|---|---|---|---|---|
| TPMT3B (G460A) | 3A1F Tag (SEQ ID NO:9) | 100 uM | 0.1 | 400 |
| TPMT3C (A719G) | 3A2F Tag (SEQ ID NO:10) | 100 uM | 0.1 | 400 |
| H₂O | | | 0.2 | 800 |

The above extension primers are tagged with unique Tag-It DNA Sequence™ (Luminex).

The biotin-ddATP/ddNTP mix for the A reaction was prepared according to table 8 below.

TABLE 8

Biotin-ddATP/ddNTP mix for A reaction

| Reagent | Concentration | Volume (μL) for 1 rxn | Volume (μL) for 120 rxns (full plate) |
|---|---|---|---|
| Biotin-ddATP | 1 mM | 0.1 | 12 |
| ddCTP | 1 mM | 0.5 | 60 |
| ddGTP | 1 mM | 0.5 | 60 |
| ddTTP | 1 mM | 0.1 | 12 |
| Total | | 1.2 | 144 |

The primer extension master mix for the A reaction was prepared according to table 9 below.

TABLE 9

Primer Extension Master Mix for A reaction

| Reagent | 1 Rxn (μL) | Full Plate 112 Rxns (μL) |
|---|---|---|
| 10X PCR Buffer (20 mM Mg++) | 2.0 | 224 |
| Biotin-ddATP/ddNTP mix | 1.2 | 134.4 |
| PE Primer Mix for A reaction | 0.4 | 44.8 |
| H₂O | 8.15 | 912.8 |
| Mixture Total | 11.75 | 1,316 |

7.5 μL of SAP/ExoI treated sample was added to 11.5 μL PE Master Mix for A Reaction and 0.75 μL Fast Start Taq (Roche). The thermal cycler conditions for the primer extension reaction were as follows:

TABLE 10

Primer extension reaction conditions

| Step | Temperature | Time |
|---|---|---|
| 1 | 96° C. | 2 min. |
| 2 | 95° C. | 30 sec |
| 3 | 50° C. | 30 sec |
| 4 | 60° C. | 30 sec |
| 5 | Go to Step 2 | 50 Cycles |
| 6 | 4° C. | 5 min |
| 7 | 4° C. | Hold |

G Reaction

The primer extension primer mix for the G reaction was prepared according to table 11 below.

TABLE 11

Primer extension (PE) primer mix for G reaction

| Mutation | Primer | Concentration (μM) | Volume (μL) for 1 rxn | Volume (μL) for 4000 rxns |
|---|---|---|---|---|
| TPMT*2 | 2F Tag (SEQ ID NO:7) | 100 uM | 0.1 | 400 |
| TPMT*2 | 2R Tag (SEQ ID NO:8) | 100 uM | 0.1 | 400 |
| TPMP*3B (460G > A) | 3A1F Tag (SEQ ID NO:9) | 100 uM | 0.1 | 400 |
| TPMT*3C (719A > G) | 3A2F Tag (SEQ ID NO:10) | 100 uM | 0.1 | 400 |
| H₂O | | | 0.4 | 1,600 |

The above extension primers are tagged with unique Tag-It DNA Sequence™ (Luminex).

The Biotin-ddATP/ddNTP mix for G reaction was prepared according to table 12 below.

TABLE 12

Biotin-ddATP/ddNTP mix for G reaction

| Reagent | Concentration | Volume (μL) for 1 rxn | Volume (μL) for 120 rxns (full plate) |
|---|---|---|---|
| Biotin-ddGTP | 1 mM | 0.1 | 12 |
| ddCTP | 1 mM | 0.5 | 60 |
| ddATP | 1 mM | 0.5 | 60 |
| ddTTP | 1 mM | 0.1 | 12 |
| Total | | 1.2 | 144 |

The primer extension (PE) master mix for the G reaction was prepared according to table 13 below.

TABLE 13

Primer Extension Master Mix for G reaction

| Reagent | 1 Rxn (μL) | Full Plate 112 Rxns (μL) |
|---|---|---|
| 10X PCR Buffer (20 mM Mg++) | 2.0 | 224 |
| Biotin-ddGTP/ddNTP mix | 1.2 | 134.4 |
| PE Primer Mix for G reaction | 0.8 | 89.6 |
| H₂O | 7.75 | 868 |
| Mixture Total | 11.75 | 1,316 |

7.5 μL of SAP/ExoI treated sample was added to 11.5 μL PE Master Mix for G Reaction and 0.75 μL Fast Start Taq (Roche). The thermal cycler conditions for the primer extension reaction for the G reaction were the same as the conditions recited above for the A reaction.

Detection

The extension primers were captured on solid phase by hybridization of a the Tag-It DNA sequence to the corresponding Anti-Tag sequence (i.e., the complementary sequence to the tag sequence contained in the extension primer) coupled to the surface of a fluorescent-labeled microsphere. The microspheres were then subjected to flow cytometry in which the presence of labeled extension primer was detected.

5× hybridization buffer is prepared according to table 14.

TABLE 14

5X hybridization buffer

| Regents | Concentration (M) | Volume (mL) or Weight (g) |
|---|---|---|
| Tris-HCl (pH 8.0) | 1 M | 550 mL |
| Triton-100 | 100% | 4.4 mL |
| NaCl | | 64.25 g |
| H₂O | | ~440 mL* |

*The H₂O volume is an estimate, add H₂O last to the final volume of 1 L.

The Luminex 4 bead mix was prepared according to the following table. All beads were obtained from Luminex Corp. (Austin, Tex.). Each bead bottle was vortexed for 20 seconds followed by sonication for 20 seconds. Vortexing and sonication were repeated once more. The beads are light-sensitive and thus the bead solution needs to be kept away from light.

TABLE 15

Luminex 4 bead mix

| Bead Stock Solution 2.5 × 10⁵/mL (Luminex FlexMAP microsphere) | Anti-Tag-it Sequence | 1 Rxn (µL) | Full Plate X112 Rxn (µL) |
|---|---|---|---|
| 031 (Cat. No. L-100-031) | 5'AGTTGATTGAAAAGT GAA-3' (SEQ ID NO:25) | 9 | 1,000 |
| 065 (Cat. No. L-100-065) | 5'AAAGGTAAGATTATT GATGAAAAG-3' (SEQ ID NO:26) | 9 | 1,000 |
| 095 (Cat. No. L-100-095) | 5'TTAGTGTAGTAAGTT TAAAGTGTA-3' (SEQ ID NO:27) | 9 | 1,000 |
| 012 (Cat. No. L-100-012) | 5'AAAGAAAGAAAGAAA GAAAGTGTA-3' (SEQ ID NO:28) | 9 | 1,000 |
| ddH2O | | 4 | 480 |
| Total | | 40 | 4,480 |

The bead hybridization was performed as follows. A bead hybridization solution was prepared according to the following table.

TABLE 16

Bead hybridization solution

| Reagent | 1 Rxn (µL) | 112 Rxns Per Plate(µL) |
|---|---|---|
| 4 Beads Mix | 40 | 4,480 |
| 5X Hyb. Buffer | 10 | 1,120 |
| Total | 50 | 5,600 |

50 µL of the bead hybridization solution was added to each appropriate well of an ABI Optical 96-well plate. 5 µL of the Primer Extension product (from Example 3) was added. The plate was sealed but not vortexed or centrifuged. (Centrifugation of the bead hybridization plate will cause the beads to form a pellet at the bottom of the plate and not hybridize to the primer extension product.) The plate was placed in a thermal cycler and subjected to the conditions according to table 17 below.

TABLE 17

Bead hybridization conditions

| Step | Temp. | Time |
|---|---|---|
| 1 | 96° C. | 2 min. |
| 2 | 37° C. | 1 hour |
| 3 | 37° C. | Hold |

The wash solution was prepared according to table 18.

TABLE 18

Wash solution (1X Hybridization Buffer)

| Reagent | 1 Rxn (µL) | 112 Rxn Full Plate (µL) |
|---|---|---|
| ddH2O | 120 | 13,440 |
| 5X Hyb. Buffer | 30 | 3,360 |
| Total | 150 | 16,800 |

The reporter solution of streptavidin R-phycoerythrin (SA-PE) conjugate was prepared by vortexing the tube of SA-PE for 2-5 seconds. The appropriate amount of SA-PE was added to appropriate 1× hybridization buffer. SA-PE is light sensitive so exposure to light should be limited and the solution stored in the dark until ready to use. Prepare 5-10 minutes before use.

TABLE 19

Reporter solution

| Loading Mix | 1 Rxn (µL) | Full Plate x112 Rxn |
|---|---|---|
| 1X Hybridization Buffer | 150 | 16800 |
| SA-PE | 0.4 | 44.8 |
| Total | 150.4 | 16,844.8 |

The bead hybridization plate was removed from the thermal cycler. The plate was sealed and spun at 3000 RCF (not rpm) for 5 minutes in a microplate centrifuge. The plate was inverted over paper towels and tapped to remove excess liquid. 150 µL of wash solution was added to each well. The plate was sealed and vortexed for 10 seconds. Vortexing was repeated two more times. The plate was sealed and spun at 3000 RCF (not rpm) for 5 minutes in a microplate centrifuge. The plate was inverted over paper towels and tapped to remove excess liquid. 150 µL of reporter solution was added to each well. The 150 µL solution was carefully pipetted up and down 8 times. The solution was transferred to a new Falcon DB 96-well plate. The plate was placed in the dark for 15 minutes then placed on the Luminex 100 IS instrument. The results of the detection by the Luminex 100 IS instrument were correlated to the genotype at each mutation position as follows.

TABLE 20

Detection results for the A Reaction

| Primer | ΔMFI* | Wild-type (Wt) or mutation | Genotypes |
|---|---|---|---|
| 3A1F Tag | >400 | Mutation | 460A |
| 3A2F Tag | >800 | Wt | 719A |

*Δ MFI is the MFI of samples with DNA minus the MFI of samples without DNA control.

TABLE 21

Detection results for the G Reaction

| Primer | ΔMFI* | Wild-type (Wt) or mutation | Genotypes |
|---|---|---|---|
| 2AF Tag | >800 | Wt | 238G |
| 2AR Tag | >800 | Mutation | 238C |
| 3A1F Tag | >800 | Wt | 460G |
| 3A2F Tag | >800 | Mutation | 719G |

Cell samples processed by method "A" above and diluted 1:125 with water prior to use in PCR, showed robust amplification (as determined by gel electrophoresis) and worked well in the single nucleotide primer extension step.

Cell samples processed by method "B" above and diluted 1:5 prior to PCR showed amplification was not robust (as determined by gel electrophoresis) and the single nucleotide primer extension step did not work. Cell samples processed by method "B" above and diluted 1:25 and 1:125 prior to PCR showed good amplification (as determined by gel electrophoresis) and worked well in the subsequent single nucleotide primer extension step.

Example 2

Factor XI Deficiency Assay Using Processed Whole Blood as the Nucleic Acid Template for Amplification Processed whole blood samples provided the template for a triplex PCR reaction used to amplify fragments of DNA containing Type I and IV mutations, the Type II mutation, and the Type III mutation in the Factor XI gene. The amplification reaction was followed by a single nucleotide primer extension reaction to detect the presence of mutations.

Whole blood samples were prepared for use in the Factor XI assay by the following two methods:

A) Whole blood samples were processed by adding 100 μL of DNA preserving solution from the Oragene™ DNA Self-Collection Kit (DNA Genotek, Ottawa, Ontario, Canada) to 50 μL whole blood. The samples were mixed and 6 μL Purifier solution (DNA Genotek, Inc.) was added. Samples were centrifuged and the supernatant collected. The supernatant was serial diluted in water the following ratios 1:5, 1:25, 1:125, 1:625, and 1:3125.

B) Whole blood samples were processed by adding 80 μL of DNA preserving solution from the Oragene™ DNA Self-Collection Kit (DNA Genotek, Ottawa, Ontario, Canada) to 40 μL whole blood. Samples were centrifuged and the supernatant collected. The supernatant was diluted 1:5 in water.

The following primers were used in the triplex PCR reaction.

TABLE 22

Factor XI PCR primers

| Location in GenBank Acc. No. AY191837 | Primer Name | Sequence |
|---|---|---|
| 10660-10682 | F11F1 | 5'-*TGT AAA ACG ACG GCC AGT* GCT TGC AAC AAA GAC ATT TAT GT-3' (SEQ ID NO:11) |
| 10856-10835 | F11R1 | 5'-*CAG GAA ACA GCT ATG ACC* TTC ATC GAC CAC TCG AAT GTC C-3' (SEQ ID NO:12) |
| 16730-16747 | F11F2 | 5'-*TGT AAA ACG ACG GCC AGT* AGG GAG GGT CTC ACT CTG-3' (SEQ ID NO:13) |
| 16879-16862 | F11R2 | 5'-*CAG GAA ACA GCT ATG ACC* CGG ACG GCA TTG GTG CAC-3' (SEQ ID NO:14) |
| 24311-24335 | F11F3 | 5'-ATA ACC CAT AAG ATG ATC TGT GCC G-3' (SEQ ID NO:15) |
| 24426-24405 | F11R3 | 5'-CCC CAA CGC ATT AAG CAT TCC AA-3' (SEQ ID NO:16) |
| 24351-24400 | Control IVS V5 Mutant | 5'-GGA AGG ACG CTT GCA AGA TAA CAG AGT GTT CTT AGC CAA TGG AAT ATA TG-3' (SEQ ID NO:17) |
| 24400-24379 24364-24341 | Control Del V5 | 5'-CAT ATA TTC CAT TGG CTA AGA A GCA AGC GTC CTT CCC TCC TTC CCT-3' (SEQ ID NO:18) |

Italicized bold sequences are linkers and not part of GenBank sequence.

A Master mix of Factor XI was prepared according to table 23 below.

TABLE 23

5X solution of Factor XI primer mix

| Primer (100 μM) | Volume per reaction (μL) | Concentration Final solution (μM) |
|---|---|---|
| 10X buffer with MgCl₂ (Roche) | 1.5 | 1X |
| 25 mM dNTP | 0.1 | 159.2 |
| F11F1 (SEQ ID NO:11) | 0.03 | 0.2 |
| F11R1 (SEQ ID NO:12) | 0.03 | 0.2 |
| F11F2 (SEQ ID NO:13) | 0.03 | 0.2 |
| F11R2 (SEQ ID NO:14) | 0.03 | 0.2 |
| F11F3 (SEQ ID NO:15) | 0.06 | 0.40 |
| F11R3 (SEQ ID NO:16) | 0.06 | 0.40 |
| 5X GC Rich solution (Roche) | 0.75 | |
| dH₂O | 9.71 | |
| Total | 12.3 | |

A 15 μL reaction containing 12.3 μL Factor XI master mix, 1.2 μL MgCl₂, 0.2 μL Taq polymerase (FaststarTaq, 5 U/μL) and 2 μL of diluted, processed DNA-containing sample or control DNA was run under the following PCR conditions.

TABLE 24

PCR amplification conditions

| Step | Temperature | Time |
|---|---|---|
| 1 | 95° C. | 5 min. |
| 2 | 94° C. | 15 sec |
| 3 | −0.5° C./sec | to 58° C. |
| 4 | 58° C. | 20 sec. |
| 5 | +0.3° C./sec | to 72° C. |
| 6 | 72° C. | 30 sec. |
| 7 | +0.5° C./sec | to 94° C. |
| 8 | go to step 2 | 33 times* |
| 9 | 72° C. | 5 min. |
| 10 | 4° C. | Hold |

The expected sizes of the amplicon for each primer pair are as reported in Table 25.

TABLE 25

Factor XI gene amplicons.

| Primer pair | Target region of gene | Mutation(s) Examined | Amplicon Size (bp) |
|---|---|---|---|
| F11F1, F11R1 | Exon 5 | E117X | 235 |
| F11F2, F11R2 | Exon 9 | F283L | 186 |
| F11F3, F11R3 | Exon14/Intron 14 | IVS14N G > A; IVS14del14 | 117 |

After PCR was complete, the samples are treated with CIAP (calf intestinal alkaline phosphatase) and Exo I (exonuclease I). A fresh CIAP/ExoI cocktail is prepared prior to each use according to table 26 below.

TABLE 26

CIAP/ExoI cocktail

| Reagent | Volume (µL) for 1 reaction |
|---|---|
| CIAP (1 unit/µL) | 2.0 |
| Exo I (10 unit/µL) | 0.2 |
| Sterile H₂0 | 12.8 |
| Total | 15.0 |

3 µL of PCR product was added to 15 µL of the CIAP/ExoI cocktail and then incubated at 37° C. for 2 hours, 75° C. for 15 minutes then chilled to 4° C. and stored at 2-10° C. until use.

The single nucleotide primer extension reaction was performed using the ABI PRISM® SNaPshot® Multiplex Kit (Applied Biosystems) and the following extension primers.

TABLE 27

Factor XI extension primers.

| Location in GenBank Acc. No. AY191837 | Primer Name | Sequence |
|---|---|---|
| 10739-10764 (Rev) | E117X | 5'-GTC ATC CGT GCA TCT TTC TTG GCA TT-3' (SEQ ID NO:17) |
| 16772-16802 | F283L | 5'-CTG CCA TTC TTC ATT TTA CCA TGA CAC TGA T-3' (SEQ ID NO:18) |
| 24400-24369 | IVS14N G > A | 5'-TTT TTT TTT TCA TAT ATT CCA TTG GCT AAG AAC ACT CTG TTA-3' (SEQ ID NO:19) |
| 24345-24364 | IVS14del14 | 5'-AAG GAG GGA AGG ACG CTT GC-3' (SEQ ID NO:20) | italicized bold sequences are linkers and not part of Genebank sequence.

The primer extension primer mix was prepared according to table 28 below.

TABLE 28

Primer extension (PE) primer mix

| Primer | Concentration (µM) | Volume (µL) for 1 rxn | Final conc. (µM) |
|---|---|---|---|
| E117X | 100 uM | 0.2 | 0.2 |
| F283L | 100 uM | 0.2 | 0.2 |
| IVS14N G > A | 100 uM | 0.5 | 0.5 |
| IVS14del14 | 100 uM | 0.2 | 0.2 |
| Sterile dH₂O | | 0.89 | |
| | | 1.0 | |

The primer extension (PE) master mix was prepared according to table 29 below.

TABLE 29

Primer Extension (PE) Master Mix

| Reagent | Volume/Rxn (µL) |
|---|---|
| SNaPshot Ready Mix (contains AmpliTaq DNA Polymerase, fluorescent labeled ddNTPs) (Applied Biosystems) | 2.0 |
| 5X ABI sequencing buffer | 2.0 |
| PE Primer Mix | 1.0 |
| H₂O | 2.0 |
| Mixture Total | 7.0 |

3 µL of CIAP/ExoI digested PCR product was added to 7.0 µL PE Master Mix. The thermal cycler conditions for the primer extension reaction were as follows.

TABLE 30

Primer extension reaction conditions

| Step | Temperature | Time |
|---|---|---|
| 1 | 95° C. | 2 min |
| 2 | 95° C. | 20 sec |
| 3 | 60° C. | 20 sec |
| 4 | Go to Step 2 | 34 times |
| 5 | 4° C. | Hold |

1 µL of CIAP (1 U/µL) was diluted with 1 µL of water and the resulting 2 µL of diluted CIAP added to the primer extension reaction product and incubated at 37° C. for 1 hour, 95° C. for 5 minutes then chilled to 4° C. and stored at 2-10° C. until use.

The CIAP digested products containing fluorescently labeled extension primers were run on an ABI PRISM 3100 Genetic Analyzer wherein the size of the oligonucleotide was determined and the incorporated fluorescent label detected and identified.

The expected peak size and color (for wild type and mutant alleles) for each labeled extension primer, as detected on the ABI 3100 genetic analyzer is as follows:

TABLE 31

Expected peak size and color for wild type and mutant alleles

| | | | Wild type allele | | | Mutant allele | | |
|---|---|---|---|---|---|---|---|---|
| SNP | Primer size (bp) | Location | Extended nucleotide | Color | Size (bp)* | Extended nucleotide | Color | Size (bp)* |
| IVS14del14 | 20 | Exon14/Intron14 | A | Green | 24-26 | T | Red | 24.5-26.5 |
| E117X | 26 | Exon 5 | G | Black | 30-32 | T | Green | 30.9-32.9 |
| F283L | 31 | Exon 9 | T | Red | 33.5-35.5 | C | Black | 31.5-33 |
| IVS14N G > A | 42 | Intron 14 | C | Black | 42.5-44.5 | T | Red | 45-46.5 |

*The size of the primer extension product is affected by mobility shift caused by the incorporated fluorescent dye labeled ddNTP.

Cell samples processed by method "A" above and diluted 1:5, 1:25, and 1:125 worked in the Factor XI assay, whereas processed samples diluted 1:625 worked minimally (i.e., only one of four samples showed amplification, as determined by gel electrophoresis), and undiluted processed samples or those diluted 1:3125 did not work. Cell samples processed by method "B" above and diluted 1:5 prior to use in PCR, showed robust amplification (as determined by gel electrophoresis) and worked well in the SNaPshot assay.

Example 3

Factor V Deficiency Assay Using Processed Whole Blood as the Nucleic Acid Template for Amplification Processed whole blood samples were assayed for the R506Q mutation in the Factor V (caused by a G to A transition at nucleotide position 1691 in the Factor V cDNA). The presence or absence of the mutation is determined using the READIT™ System (Promega Corp., Madison, Wis.) to interrogate PCR products encompassing nucleotide at position 1691.

Whole blood samples were processed by adding 80 μL of DNA preserving solution from the Oragene™ DNA Self-Collection Kit (DNA Genotek, Ottawa, Ontario, Canada) to 40 μL whole blood. Samples were centrifuged and the supernatant collected. The supernatant was diluted 1:5 in water. Diluted samples were assayed according to the Factor V assay as follows.

PCR was used to amplify a 234 bp region of the Factor V gene including the nucleotide at position 1691. A PCR Master Mix was prepared according to the following table.

TABLE 32

Factor V PCR Master Mix

| Reagent | Volume/ Rxn (μL) | Final conc. (μM) |
|---|---|---|
| 2X Universal Master Mix (Promega Corp.) | 6.88 | 1X |

TABLE 32-continued

Factor V PCR Master Mix

| Reagent | Volume/ Rxn (μL) | Final conc. (μM) |
|---|---|---|
| FV-F Thioate primer (50 pm/uL) 5'-G*A*T*GAA CCC ACA GAA AAT GAT GCC AG-3' (SEQ ID NO:21) | 0.138 | 0.25 |
| FV-R primer (50 pm/uL) 5'-GGA AAT GCC CCA TTA TTT AGC CAG GAG-3' (SEQ ID NO:22) | 0.138 | 0.25 |
| Nuclease-free dIH₂O | 5.5 | |
| Mixture Total | 12.656 | 12.656 |

"*" represents a phosphothioate linkage

2 μL diluted processed blood sample was added to 11.5 μL PCR master mix, mixed and spun down. PCR was performed using the following conditions.

TABLE 33

PCR conditions

| Step | Temperature | Time |
|---|---|---|
| 1 | 95° C. | 1 min |
| 2 | 95° C. | 20 sec |
| 3 | 60° C. | 15 sec |
| 4 | 72° C. | 15 sec |
| 5 | Go to Step 2 | 39 times |
| 6 | 72° C. | 1 min |
| 7 | 4° C. | Hold |

PCR products were digested with calf intestinal alkaline phosphatase and exonuclease I. Genotyping of the PCR products was then performed using the following interrogation probes and the READIT SNP Genotyping System (Promega Corp.) in accordance with the manufacturer's protocol.

TABLE 34

Factor V READIT System interrogation probes.

| Location in GenBank Acc. No. Z99572 | Primer Name | Sequence |
|---|---|---|
| 62902-62931 | FV WT (wild type allele) | 5'-CTT GAA GGA CAA AAT ACC TGT ATT CCT CG-3' (SEQ ID NO:23) |
| 62902-62931 | FV MUT (mutant allele) | 5'--CTT GAA GGA CAA AAT ACC TGT ATT CCT TG-3' (SEQ ID NO:24) |

Nucleotide in bold and underlined represents the base at position 1691 in the wild type and mutant sequences.

The processed samples produced good results in the READIT system assay.

Example 4

Assay for Cystic Fibrosis Gene Mutations Using Processed Whole Blood as the Nucleic Acid Template for Amplification Processed blood samples were assayed for the presence of various mutations in the CF gene using PCR-oligonucleotide ligation assay (OLA) technology. Patient genomic DNA in a sample of whole blood is amplified in a 15-plex PCR. The amplicons are then interrogated using the Cystic Fibrosis OLA ASR assay version 3.0 (Applied Biosystems) as described by Grossman et al. (Nucleic Acids Research 22:4527-34, 1994) and Spitzer et al. (Eur. Respir. J 19:374-6, 2002).

Whole blood samples were processed for use in the CF assay by the following method: whole blood samples were processed by adding 80 µL of DNA preserving solution from the Oragene™ DNA Self-Collection Kit (DNA Genotek, Ottawa, Ontario, Canada) to 40 µL whole blood. Samples were centrifuged and the supernatant collected. The supernatant was diluted 1:5, 1:25, and 1:125 in water.

Diluted samples were assayed using the Cystic Fibrosis OLA ASR assay according to the manufacturer's protocol.

The samples processed according to the method above and diluted 1:5 produced the best results the CF OLA assay, whereas samples diluted 1:125 produced the worst results of the three dilution factors.

Unless otherwise defined, all technical and scientific terms used herein have the same meaning as commonly understood by one of ordinary skill in the art to which this invention belongs. All nucleotide sequences provided herein are presented in the 5' to 3' direction.

The inventions illustratively described herein may suitably be practiced in the absence of any element or elements, limitation or limitations, not specifically disclosed herein. Thus, for example, the terms "comprising", "including," "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed.

Thus, it should be understood that although the present invention has been specifically disclosed by preferred embodiments and optional features, modification, improvement and variation of the inventions embodied therein disclosed may be resorted to by those skilled in the art, and that such modifications, improvements and variations are considered to be within the scope of this invention. The materials, methods, and examples provided here are representative of preferred embodiments, are exemplary, and are not intended as limitations on the scope of the invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

In addition, where features or aspects of the invention are described in terms of Markush groups, those skilled in the art will recognize that the invention is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

Other embodiments are set forth within the following claims.

That which is claimed is:

1. A method for amplifying nucleic acids from a sample, said method comprising, contacting said sample with a solution comprising a chelating agent, a denaturing agent, and a buffering agent to form a modified sample, wherein said solution has a pH between about 5 and about 11, and using the modified sample as a template in a nucleic acid amplification reaction, wherein said sample is blood plasma or serum.

2. The method of claim 1, wherein said sample is blood plasma.

3. The method of claim 1, wherein said sample is blood serum.

4. The method of claim 1, wherein said pH is between about 7 and about 10.

5. The method of claim 1, wherein said pH is about 8.

6. The method of claim 1, wherein said chelating agent is selected from the group consisting of: ethylenediamine tetraacetic acid (EDTA), cyclohexane diaminetetraacetate (CDTA), diethylenetriamine pentaacetic acid (DTPA), tetraazacyclododecanetetraacetic acid (DOTA), tetraazacyclotetradecanetetraacetic acid (TETA), desferrioximine, and analogs thereof.

7. The method of claim 1, wherein said denaturing agent is selected from the group consisting of a detergent, a chaotrope, or an alcohol.

8. The method of claim 1, wherein said denaturing agent is selected from the group consisting of: urea, sodium dodecyl sulfate, dodecyl sulfate, guanidinium chloride, guanidinium thiocyanate, perchlorate, methanol, ethanol, n-propanol, isopropanol, n-butanol, trifluoroethanol, phenol, and 2,6-di-tert-butyl-4-methylphenol.

9. The method of claim 1, wherein said denaturing agent is sodium dodecyl sulfate.

10. The method of claim 1, wherein said solution further comprises a reducing agent.

11. The method of claim 1, wherein said reducing agent is selected from the group consisting of: ascorbic acid and 2-mercaptoethanol.

12. The method of claim 1, wherein said solution further comprises an antimicrobial agent.

13. The method of claim 1, wherein said solution further comprises a ribonuclease inhibitor.

14. The method of claim 1, wherein said nucleic acid amplification comprises polymerase chain reaction (PCR).

15. The method of claim 1, wherein said nucleic acid amplification comprises reverse transcription polymerase chain reaction (RT-PCR).

* * * * *